(12) United States Patent
Donner (10) Patent No.: US 9,574,988 B2
(45) Date of Patent: Feb. 21, 2017

(54) SENSOR AND METHODS FOR MEASURING PARTICLES IN MEDIA

(71) Applicant: Bernd Donner, Freyming (FR)

(72) Inventor: Bernd Donner, Freyming (FR)

( * ) Notice: Subject to any disclaimer, the term of this patent is extended or adjusted under 35 U.S.C. 154(b) by 233 days.

(21) Appl. No.: 14/410,340

(22) PCT Filed: Jun. 17, 2013

(86) PCT No.: PCT/EP2013/062495
§ 371 (c)(1),
(2) Date: Dec. 22, 2014

(87) PCT Pub. No.: WO2013/189879
PCT Pub. Date: Dec. 27, 2013

(65) Prior Publication Data
US 2015/0369722 A1 Dec. 24, 2015

(30) Foreign Application Priority Data
Jun. 21, 2012 (DE) .................. 10 2012 105 379

(51) Int. Cl.
*G01N 15/14* (2006.01)
*G01N 21/94* (2006.01)
(Continued)

(52) U.S. Cl.
CPC .......... *G01N 15/14* (2013.01); *G01N 15/1031* (2013.01); *G01N 15/1459* (2013.01);
(Continued)

(58) Field of Classification Search
CPC ............... G01N 2015/0023; G01N 2015/0026; G01N 2015/003; G01N 2015/0034; G01N 2015/0038; G01N 2015/0042; G01N 2015/0046; G01N 2015/0049; G01N 2015/0053; G01N 2015/0057; G01N 2015/0065; G01N 2015/0073; G01N 2015/0074; G01N 2015/008; G01N 2015/0084; G01N 2015/0088; G01N 2015/0092; G01N 2015/0216; G01N 2015/0222; G01N 2015/0238; G01N 2015/0244; G01N 2015/025; G01N 2015/03; G01N 2015/035; G01N 2015/0668; G01N 2015/0693; G01N 2015/1062; G01N 2015/1081; G01N 2015/1087; G01N 2015/1093; G01N 2015/1447; G01N 2015/144; G01N 2015/145; G01N 15/02; G01N 15/0205; G01N 15/0211; G01N 15/0227; G01N 15/0656; G01N 15/10; G01N 15/1031; G01N 15/14; G01N 15/1404; G01N 15/1434; G01N 15/1436; G01N 15/1456; G01N 15/1459; G01N 15/1463; G01N 15/1465; G01N 15/1468; G01N 15/147; G01N 15/1472; G01N 15/1475; G01N 2021/8578; G01N 2021/4769; G01N 2021/513; G01N 2021/8405; G01N 21/47; G01N 21/4738; G01N 21/4795; G01N 21/49; G01N 21/51; G01N 21/53; G01N 21/532; G01N 21/534; G01N 21/84; G01N 21/85; G01N 21/88; G01N 21/8803; G01N 21/8806; G01N 21/90; G01N 21/9009; G01N 21/9018; G01N 21/9027; G01N 21/94
See application file for complete search history.

(56) References Cited

U.S. PATENT DOCUMENTS 4,651,091 A * 3/1987 Chambers ................ G01N 3/56
324/204
4,725,140 A * 2/1988 Musha .................... G01N 21/21
356/336
(Continued)

FOREIGN PATENT DOCUMENTS

EP 0984278 A1 3/2000
WO 9740360 A1 10/1997
WO 2007121879 A1 11/2007

*Primary Examiner* — Gordon J Stock, Jr.
(74) *Attorney, Agent, or Firm* — Laurence A. Greenberg; Werner H. Stemer; Ralph E. Locher (57) ABSTRACT

A sensor for measuring particles in contaminated media contains an optically transparent measuring cell, through
(Continued)

which a capillary tube for conducting and measuring a medium passes, an optical detector, and a magnetic detector. The measuring cell is cylindrical, the capillary tube extends coaxially in the measuring cell and an inspection space is arranged in a center of the measuring cell. On the inspection space an optical lens system having a light source and at least one optical detector is focused. Differential coils for producing and detecting a coaxial alternating magnetic field form the magnetic detector on the shaft of the measuring cell, which differential coils are controlled in such a way that the alternating magnetic field is canceled out in the inspection space.

27 Claims, 9 Drawing Sheets

(51) Int. Cl.
  *G01N 21/88* (2006.01)
  *G01N 21/85* (2006.01)
  *G01N 21/53* (2006.01)
  *G01N 21/49* (2006.01)
  *G01N 15/10* (2006.01)

(52) U.S. Cl.
  CPC ............ *G01N 21/49* (2013.01); *G01N 21/53* (2013.01); *G01N 21/85* (2013.01); *G01N 21/88* (2013.01); *G01N 21/94* (2013.01); *G01N 2015/1087* (2013.01)

(56) References Cited

U.S. PATENT DOCUMENTS

| | | | |
|---|---|---|---|
| 5,001,424 A | 3/1991 | Kellett et al. | |
| 5,173,600 A * | 12/1992 | Fillion | F16N 29/00 250/227.11 |
| 5,790,246 A | 8/1998 | Kuhnell et al. | |
| 6,103,113 A * | 8/2000 | Saho | B03C 1/035 209/232 |
| 6,151,108 A | 11/2000 | Kwon et al. | |
| 7,788,969 B2 * | 9/2010 | Verdegan | G01N 15/0205 73/53.01 |
| 8,212,556 B1 * | 7/2012 | Schwindt | G01R 33/26 324/301 |
| 2004/0045368 A1 * | 3/2004 | Schoeb | G01F 1/28 73/861.08 |
| 2005/0213080 A1 * | 9/2005 | Huang | G01N 21/4133 356/128 |
| 2008/0106261 A1 * | 5/2008 | Romalis | G01R 33/441 324/304 |
| 2010/0033158 A1 | 2/2010 | Dittmer et al. | |
| 2010/0297780 A1 | 11/2010 | De Theije et al. | |
| 2012/0050736 A1 * | 3/2012 | Strong | G01N 21/23 356/337 |
| 2012/0203529 A1 * | 8/2012 | Gaskin | G01N 27/74 703/9 |

* cited by examiner

SENSOR AND METHODS FOR MEASURING PARTICLES IN MEDIA

BACKGROUND OF THE INVENTION

Field of the Invention

The invention relates to a sensor for measuring particles in contaminated media, having an optically transparent measuring cell, through which a capillary tube for conducting and measuring the medium passes, an optical detector, and a magnetic detector.

For detecting particles, said particles are differentiated according to the specific type and material characteristics thereof. Defined as particles are all material components located in a spatial detection region (inspection space), except for the material that constitutes the medium in which the particles are contained. The particles can be present here in solid, liquid or gaseous form or in the form of a vacuum in the medium. The medium consists of a homogeneous material with a sufficient transparency for the quasi magnetostatic or electromagnetic alternating fields that are used in the detection to pass through.

Here, magnetically active particles in the size region of interest are detected by way of the simultaneous application of magnetic alternating fields for detecting the magnetic properties of a discrete particle located in the detection region and the application of electromagnetic alternating fields preferably in the region of the light waves for specifying the size and shape. The magnetic alternating fields necessary herefor are produced by way of coils. The magnetic fields which interact with magnetically active particles are detected using suitable detectors, such as for example coils, Hall effect detectors etc. Application of static magnetic fields is also possible in principle. However, this has the disadvantage that, on account of the directional forces acting on the particles, said particles are kept in place in the detection region and could lead to a destruction of the overall system. In addition, this method can be used to detect only ferromagnetic particles. Non-iron metals have a permeability which is too low to attain evaluable signal magnitudes when they are exposed to static magnetic fields. Detecting them is therefore based on the dynamic induction of alternating currents and the effect caused thereby on the magnetic alternating fields causing them. For this reason, this variant is more suitable for applications in which the medium in which the particles are enclosed has a solid state (for example minerals, ores etc.).

A majority of the samples occurring in practice cannot be measured on account of insufficient capability of the analysis devices. This is due to the simple configuration of the inspection space, which is always shaped to be largely prismatic. It is possible here to distinguish between thin flat "curtain-type" cross sections and column-type round or square cross sections. The reason for the insufficient detectability is the characteristic curve which is relatively large and often in the shape of a parabola of up to 100% of the measurement region and the inspection space volume, which is large relative to the flow cross section of the measurement volume, which in the case of an increase in particle concentrations, in particular of smaller particles, leads to early coincidences. Coincidences occur if more than a single particle is present in the inspection space at the same time and thus contributes to the signal generation. This is countered by the method according to the prior art in that the suspensions to be investigated are diluted through mixing in of fluids with a known particle concentration that is as low as possible until the particle concentration is reduced to a range in which the sensors work again. This method is very complicated and is additionally suitable only for laboratory investigations and is not applicable in principle for online measurements with fixedly installed sensors.

Also for this reason, no particle sensors are offered at the moment that cover the complete range of the particle concentrations, as are specified for example in ISO4406 or ISO16232.

In particular in the case of fluids which are in use for a relatively long time, the proportion of oil ageing products increases. One consequence of this is that the opacity can increase to such an extent that the fluid flow can no longer be sufficiently penetrated by optical means, and thus the intensity loss can no longer be compensated for. This has a particularly disadvantageous effect in sensors which bring about the inspection space modeling using vignetting and are thus subject to high light loss. It is additionally necessary to compensate for this light loss by way of stronger subsequent amplification, which in turn has a disadvantageous effect on the achievable signal-to-noise ratio and thus on the lower detection limit of the particle size and on the bandwidth in the frequency region. By lowering the frequency bandwidth, a proportional decrease of the achievable flow rate of the fluid in the measurement volume occurs, which has a secondary negative effect in the form of an increased susceptibility to soiling and even to blockage.

A more detailed analysis of the contamination with respect to its material characteristics (for example the differentiation between metal and non-metal or air) is not available in the form of a compact, miniaturized sensor which is worth buying for mass applications. If a heterogeneous particle distribution according to its substance (for example quartz, air, soot and additives) occurs, as is often the case in practice, alarm limits are exceeded in cases where components which are not harmful for the system are present, or vice versa, are not reached in the case of harmful particles being present, with the respectively negative consequences.

In specific applications, fatal incorrect measurements result from the lack of differentiation of the material composition of the particles and also from the "empirical" calibration which is not traceable to SI units. In addition to the disadvantageous effects of the resulting false evaluation of the existing contamination on the system or machine, substantial reservations occur in qualifying the sensors for routine or serial use.

In the case of operation-technical monitoring of a system, often the necessity arises to establish corresponding conditioning of the fluid parameters for the sensors using additional functional elements, such as for example flow divider, throughflow regulator, check valves, air solution sections with a frequently uncertain operational method. Their correct functioning cannot be ensured under all operating conditions, which results in false results or incorrect measurements which, in the worst case, are not immediately recognized as such with the corresponding negative consequences for the system to be monitored.

In analysis devices which are intended to be operated at high pressure connections, the fluid exit of the device must be connected to a tank line or, if not present, the exiting fluid must be collected and subsequently discarded. Direct recycling into the fluid circuit often does not occur on account of a lack of pressure stability of the hydraulic internal components.

Large dead volumes inside sensors cause various problems:

Large volumes of the hydraulic connections or feed lines for dissolving gas bubbles in the fluid of typical sensors and arrangements falsify the measurement results by contamination and slow mixing with the in each case previous sample, on account of which the indication is delayed.

In addition, "dirt pockets" can form there which, with varying operating conditions such as pressure surges or fluctuating volume flows, suddenly join the fluid flow of the sensor and can trigger phantom alarms on account of false measurement values.

Large volumes require large sample quantities and intermediate flushing processes in order to obtain stable measurement values.

Described in the international patent application WO 2007/121879 A1 is a method and a sensor apparatus for determining the particle numbers in an oil volume, wherein an optical, a magnetic and a dielectric sensor are arranged in a measurement cell. The optical sensor is a simple light barrier in the case of which the transmitted light is quantified.

Patent application US 2010/0297780 A1 discloses a sensor for measuring particles in contaminated media, in which an optical sensor and/or a magnetic sensor can be used. A specific configuration of said sensors is not given. A magnetic differential alternating field for influencing particles is not given.

Patent application US 2010/0033158 A1 discloses a method for determining clumps of magnetic particles in a medium, in which magnetic sensors can also be used. A specific configuration of said sensors is not given. A magnetic differential alternating field for influencing particles is not given.

The known prior art only describes sensors, the inspection spaces of which do not coincide or do not overlap such that the respective sensitivity reaches its maximum at the same time at the same site. It is therefore not possible to assign in each case all detectable properties to one discrete particle.

Seals integrated in sensors and other materials wetted by the fluid are not resistant to all used fluids. This forces the customer and the manufacturer in equal terms to multiply the type variants and to use corresponding logistics with the necessary warehousing and corresponding multiplication of the capital commitment.

Required for the measurement of the most important fluid parameters is a large number of discrete individual sensors (in each case one sensor for each measurement variable), which not only need to be conditioned in fluid-technological terms and be connected in an interconnection with a hydraulic block, but additionally also must be combined together electrically and in terms of software. To this end, in the field of electronics, additional components and software are also necessary. When using various sensors with fluid-technological conditioning, high investments are necessary on account of the interconnection. As a result, the sensors offered on the market for already known mass applications are too expensive, such as for example for:

plastics injection molding machines in the medium and lower price classes, diesel engines for mobile hydraulics and maritime applications, automatic transmissions for commercial vehicles and high-quality passenger vehicles, hydraulics components such as pumps, proportional valves, cylinders etc., gas turbines.

The regular calibration of the sensors which is necessary as measurement means is a large problem for the user:

Calibration of the sensors is not traceable to SI units.

Relevant calibration methods are very expensive, imprecise, time consuming (up to 7 hours, plus disassembly and reinstallation and transport).

Calibration devices are complicated apparatuses and require constant monitoring and servicing by highly qualified technical staff.

The necessary recalibration of the sensors in fixed time intervals is complicated and time-consuming and is another count against the spread of the measurement technology. Customers are in principle not able to carry out calibrations themselves. A small range of functions forces the user to integrate various components from in some cases a plurality of suppliers. In the process, the user will encounter both the problems of system responsibility in the case of problems occurring with incompatibilities and the resulting acceptance of liability.

BRIEF SUMMARY OF THE INVENTION

It is the object of the invention to disclose an apparatus and a method for measuring particles in media which avoid said disadvantages from the prior art.

This object is achieved using an apparatus and a method according to the independent claims.

Advantageous embodiments of the invention are described in the dependent claims.

The sensor according to the invention for measuring particles in contaminated media has an optically transparent measurement cell through which a capillary tube for conducting and measuring the medium passes. At least one optical detector and one magnetic detector are arranged at the measurement cell.

The measurement cell in this case is cylindrical, and the capillary tube extends coaxially inside it. In the center of the capillary tube is an inspection space, on which an optical lens system with a light source and at least one optical detector is focused. Located on the shaft of the measurement cell are differential coils for generating and detecting a coaxial magnetic alternating field, which differential coils form the magnetic detector. They are actuated such that the magnetic alternating field in the center of the inspection space is canceled.

The measurement cell is configured to be pressure-stable, preferably made of glass. A capillary volume which is advantageously configured in a flow-technological manner has a round cross section without cross-section jumps at component transitions before and in the region around the inspection space with respect to undisturbed laminar flow and at a minimum volume of only a few mm$^3$. As a result, high volume flows and a high response rate of the sensor are achieved. The coaxial capillary tube therein has a round cross section of typically 1 to 2 mm, but can—depending on the application—also be dimensioned to be larger or smaller. The inspection space therefore also has this maximum size.

The measurement cell is accommodated coaxially in a cylindrical housing, and the medium flows into the capillary tube through a front-end opening and leaves at the end of the capillary tube perpendicular to the cylinder wall of the housing through a duct. The housing is preferably configured such that it can be inserted into a standard hole of a hydraulic device.

While for many sensors such as for example pressure or temperature sensors on account of the principle this type of construction is obvious, since the actual sensor element enables or even requires without problem an alignment which is coaxial with the housing, the corresponding solutions in the prior art are in principle opposed by this type of embodiment because it would result in dimensions which are too extremely large, because the fluid axis (x-axis), which must be coaxial with the main axis of the housing, intersects with the relatively long optical axis (z-axis). As a result, the length of the optical axis becomes the primary factor in the minimum achievable diameter, plus the required installation space for electronic and mechanical components and a sufficiently pressure-stable housing wall, the absolute thickness of which likewise increases as the overall diameter increases. A further limiting factor is the necessity in the case of high fluid pressures to provide a correspondingly pressure-stable and thus thick transparent separation of the capillary tube from the non-pressure-resistant components of the sensor.

The cylindrical form, in the case of which the region of inlet and outlet of the fluid is separated off using a seal, is provided, at that end that is opposite the concentrically arranged inlet, with an external thread which serves for attachment, to which is connected a planar surface which is perpendicular to the main axis and serves as an abutment and depth delimitation when it is screwed into the installation space. Arranged in the region of this abutment surface is a thread undercut, which is configured such that it is suitable for receiving a seal which seals off the installation space with attached sensor toward the outside. In a further preferred embodiment, an annular depression is introduced concentrically in the abutment surface, which depression serves for receiving a corresponding sealing ring. In another embodiment, the abutment surface is provided with an annular elevation having a sharp-edged configuration of the apex forming a cup point, which leads, when the sensor is installed, to reliable sealing without a sealing element directly on the planar mating surface of the installation space.

The abutment surface is followed by a drive element, with which the force-fitted mounting of the sensor in the installation space takes place. In one preferred embodiment of the solution according to the invention, the drive element has a regular polygonal, preferably hexagonal cross section.

In a further advantageous embodiment, where particularly space-saving dimensions are important, the drive is configured in the form of a toothing introduced on a cylinder-type surface in the axial direction. Despite the low toothing depth, it is still possible therefore, using a tool which can be fitted on in the axial direction and is equipped with the corresponding mating profile, to transfer a high torque for force-fitting and form-fitting installation.

At the outermost end of the sensor, behind the drive, is the electrical connection in the form of a fixedly connected cable, preferably configured according to a known proposal or in the form of a detachable connection, preferably as a plug connector.

Optionally, an optical display is provided, which is configured in a preferred embodiment as a light guide, which aligns in axially parallel fashion light radiation emanating from a commercial single-color or multi-color LED using a spherical lens surface, and on the other end of which the light exit is redirected laterally using rotationally symmetrical prisms in cone shape.

The internal connections of the functional fluid-technological components takes place using oil ducts made by drilling, which are closed off at their side which is open toward the outside according to the invention by screwing a preferably metallic plug (but also consisting of other materials), which has at its head an uninterrupted cup point, into a threaded hole which has the corresponding internal thread, and introducing a conical recess in the region toward the external surface, which recess has a larger point angle than the conical head of the plug.

In one alternative embodiment, the threaded hole can also be drilled open cylindrically in the transition region between the cone recess and the thread with a minimum diameter corresponding to the thread diameter such that the collision volume is likewise removed and a cup point forms, which produces a gas-tight seal according to the same principle as before.

By fully screwing the plug in, the cup point is brought at its entire periphery in contact with the inner cone of the recess of the hole, and after the torque has been increased to a determinable maximum value, a gas-tight metallic connection between plug head and cone recess forms, with which the hole is fixedly closed. In one preferred embodiment, the drive of the plug consists of a hole in which a hexagon socket, a multi-tooth profile or the like is introduced, which enables flush mounting of the plug. In a further preferred embodiment, a drive body having a tapering pin is connected to the conical screw head/made in one piece therewith, which, on achieving a maximum torque which is prespecifiable owing to the dimensioning in connection with the material-specific shear strength, shears off and thus makes the connection non-detachable. Solutions of such sealing plugs according to the prior art (DE8137093) are configured such that the bolt thread ends just before or in the cone of the plug, and as a result a material collision is brought about which prevents reliable sealing despite achieving the specified maximum torque, which is why said plugs must additionally be sealed and secured using sealing compound or adhesive. These adhesives, however, are not gas-tight and are subject to ageing and instability with respect to various media, and these problems are therefore eliminated by the solution according to the invention.

To determine the media state, the pressure and temperature of the medium in the capillary tube are also evaluated. To this end, a pressure measurement apparatus is provided, which is connected to the capillary tube through holes and measures the pressure of the medium in the capillary tube. The pressure measurement apparatus can be constructed using strain gauges or the like. A temperature measurement apparatus is integrated into the particle measurement apparatus.

In the apparatus according to the invention, the electromagnetic waves are generated by way of light sources. The wavelength thereof here determines the lower detection limit of the size of a discrete particle.

For applications according to the invention with particles clearly below the wavelength, the detectors are arranged at the angle that corresponds to the Raleigh radiation generated thereby for the respective detection relative to the optical main axis of the light source. In one preferred embodiment, this arrangement is achieved by what is known as a sensor array, in which the individual sensors are arranged in a planar fashion preferably on a semiconductor chip in one (1D) or multiple rows (2D). The detectors preferably consist of optoelectronic semiconductors, for example photodiodes, the sensitivity of which is within the same wavelength region as that of the light source. This is preferably likewise represented by an optoelectronic semiconductor such as for example a light-emitting semiconductor diode. The latter can emit both incoherent and coherent light.

The excess region of the light-emitting surface of the light source is covered by a stop of corresponding configuration.

The stop is configured to be reflective for this wavelength in the direction of the light source, and thus the light density in the semiconductor is increased. As a result, only part of the photons are directly absorbed and this results in an increase in the light density at the stop exit. In a preferred embodiment of the stop, the latter is directly mounted on the semiconductor and is additionally coated on the other side with a light-absorbing layer, so as to reduce scattered light.

The optical beam shaping on which the present invention is based in the ideal case starts from a linear cross section of only one wavelength, that is to say for example a line of 1 µm width. For particles which are smaller than this line width, the equation for the maximum signal magnitude $S=ad^2$ applies. For larger particles, a linear relationship applies.

The result of this is that, on the assumption of the smallest particle with 1 µm diameter, a measurement region of at least 60 dB results, simply by using the linear characteristic curve region. As a result, the measurement region is 1-1000 µm, that is to say more than 30 times that of conventional sensors.

At the same time, the linear inspection space contour effects a minimization of the volume thereof, which considerably increases the discretely evaluable particle density.

In another embodiment, the inspection space is narrowed in the direction of the optical axis to reduce the depth of field and in the image plane in the direction of the y-axis in the region of the coordinate origin to improve the coincidence density, preferably in hyperbolic form.

In a further embodiment, the inspection space cross section is rectangular with a minimum width. This cross section is characterized in that it largely fills the capillary tube perpendicular to the flow direction and is as narrow as possible in the flow direction. It should be at least narrowed so far that no region of constant light intensity prevails, but only an edge effect, i.e. that an inhomogeneous field is present. This means an early transition of the characteristic curve from the parabolic to the linear region. This is achieved according to the invention by the image of the light source being sharp in terms of depth in the inspection space in the flow direction, preferably with a maximum width of lambda of the relevant wavelength.

The inspection space can be segmented by targeted use of the depth of field of the transmitting and/or the receiving optics. Segmenting stops are here arranged in each case on the same optical axis. The evaluation density is thus increased further.

The inspection space is here still illuminated in linear fashion and the optical axis of the receiving optics is aligned to be perpendicular (that is to say in the flow direction). An enlarged image additionally occurs preferably by reduction of the inspection space depth, and the stop is used to set the inspection space depth (large stop aperture=low inspection space depth). Assigned to the respective object regions in the object plane (segment) is, on the image side of the optics, a detector element.

The total surface area of the shading produced by the projection can be computed easily by subsequent integration of the signal form, wherein the time axis must be correspondingly scaled. To this end, a suitable method and/or a suitable device is used to establish the flow quantity per unit time and to compute therefrom the speed of the particle, with which the necessary correlation of time and length can be established.

Besides the significantly improved measurement region, by integration, the measurement signal can detect and represent particles of practically unlimited length, that is to say fibrous particles. As a result, the measurement region dynamics relative to a prespecified equivalence diameter is still increased further.

The evaluation of the signals of the sensor includes an integrator for signal stabilization with a sample holding member. This leads to actual values for the regulation being measured only if no particle passes the inspection space. This avoids the global increase of the light intensity involved in otherwise typical execution of the regulation via a simple integrator and thus the falsification of the signal magnitude at large particle densities, which would otherwise result in a general signal enhancement and thus to a shift of the measurement region.

Calibration is carried out using traceable standards which are constructed such that, on a carrier, which is transparent for the optical radiation used and for the magnetic alternating fields, microstructures are applied by lithography, which correspond in terms of size region and form of the particles to be detected and the comparison sizes (comparison circle of identical surface area, comparison sphere of the same volume), and some control structures, with which the characteristic field parameters within the inspection space can be ascertained for adjustment. The actual calibration is carried out by translational and/or rotational movements of the calibration standard with its structures through the inspection space, wherein precisely defined interactions occur which enable calibration of the thus produced electrical sensor signals.

In a further embodiment with integrated image sensor, a one-line or multi-line image sensor structure is applied on the substrate of the standard, with which the inspection space is measured with respect to the distribution of the light intensity. By nanopositioning, resolution steps which are far below the pixel size are achieved. In particular, the limit region of the transition between pixels is used by evaluating the difference signal of neighboring pixels.

Mounted at the tip of the calibration standard is optionally a mechanical element which elastically seals the capillary tube in a form-fitting manner and, by its forward movement, displaces the undefined medium present in the capillary tube and in particular in the inspection space. Optionally, highly pure medium is resupplied by the calibration apparatus. This ensures that the calibration operation is not interrupted or falsified by any present particles.

A calibration station is provided for the calibration, into which the sensor is inserted. Therein, the calibration standard is introduced at defined heights into the capillary tube. To this end, preferably a piezomotor is used.

BRIEF DESCRIPTION OF THE SEVERAL VIEWS OF THE DRAWING

To explain the invention, exemplary embodiments are illustrated in the figures, in which.

DESCRIPTION OF THE INVENTION

Figure 1:
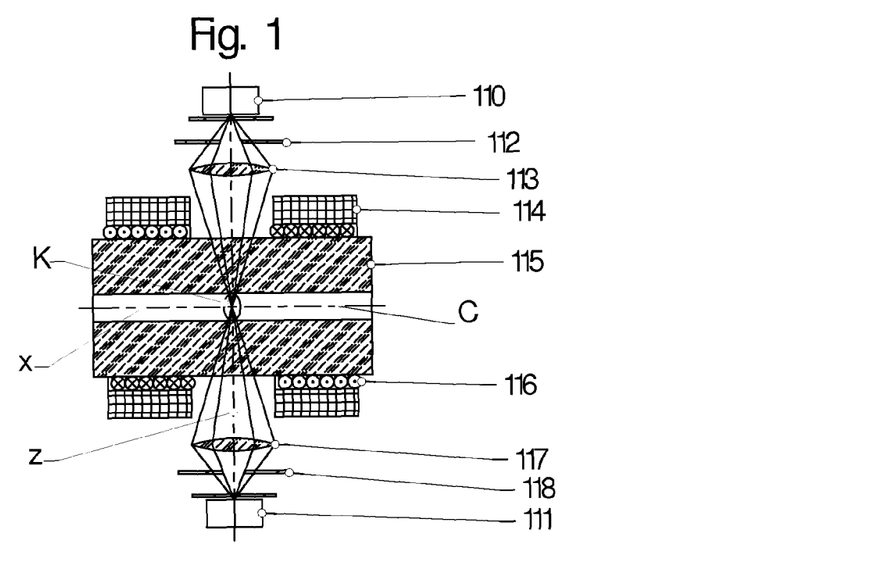
FIG. 1 shows a principle image of the sensor.

Schematically illustrated in FIG. 1 is the principle construction of the sensor. For the optical partial sensor, the light source 110, which in a particularly advantageous configuration is linear, is projected using an objective 113 onto the image plane which, in the direction of the optical axis z, intersects the longitudinal axis of the capillary tube. Here, the longitudinal axis y of the linear light source 110 is aligned to be parallel to the y-axis of the image plane and orthogonal to the longitudinal axis of the capillary tube. The x-axis of the image plane is aligned to be coaxial with the longitudinal axis of the capillary tube. The optical system of the optical detector 111 is equipped with the same components stop 118 and lenses 117 as the optical system of the light source 110.

The magnetic detector comprises two differential coils 116 which are mounted coaxially on the measurement cylinder 115. Said coils are screened toward the outside in each case via a ring core 114. The differential coils 116 produce a magnetic alternating field, the change of which is evaluated by passing magnetizable or electrically conductive particles through the inspection space K.

Figure 2:
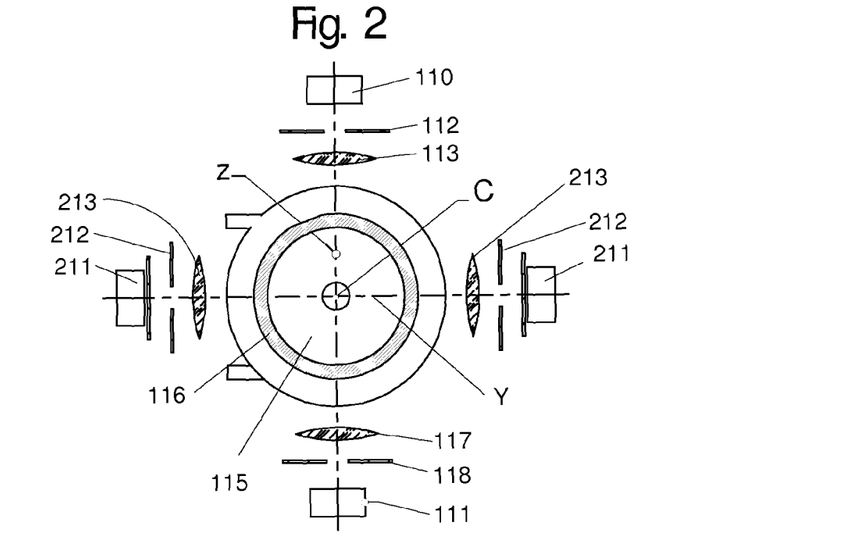
FIG. 2 shows a principle cross section of the sensor.

FIG. 2 shows a cross section through the measurement cylinder with two scattered light detectors 211. The optical system of the scattered light detectors 211 is equipped with the same components—stop 212 and lenses 213—as the optical system of the light source 110. The scattered light sensors are used to detect and evaluate specularly reflective surfaces of particles or bubbles in the medium.

Figure 3:
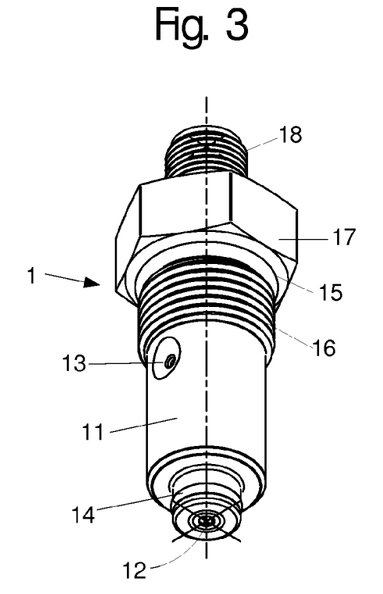
FIG. 3 shows an external view of the sensor.

FIG. 3 shows an external view of the sensor 1 with its cylindrical sensor body 11. Arranged thereon is at the bottom coaxially the inlet 12 for the medium. The outlet 13 for the medium is arranged laterally.

The sensor 1 is screwed by the screw thread 16 into a standard hole in a device using the drive 17 and sealed by the seals 14 and 15. Located at the outer end of the sensor 1 is its electrical connection.

Figure 4:
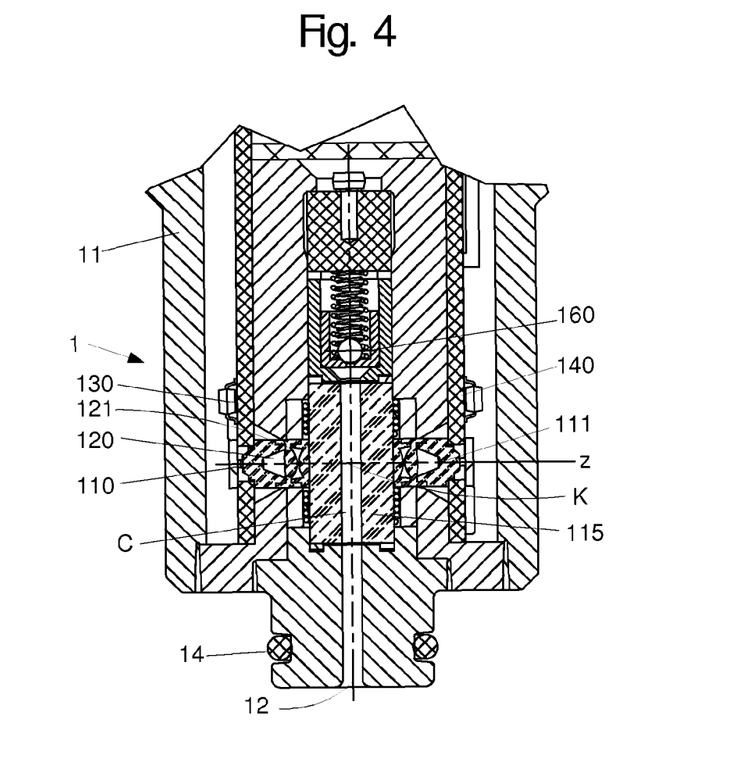
FIG. 4 shows a cross section through a simple sensor.
Figure 5:
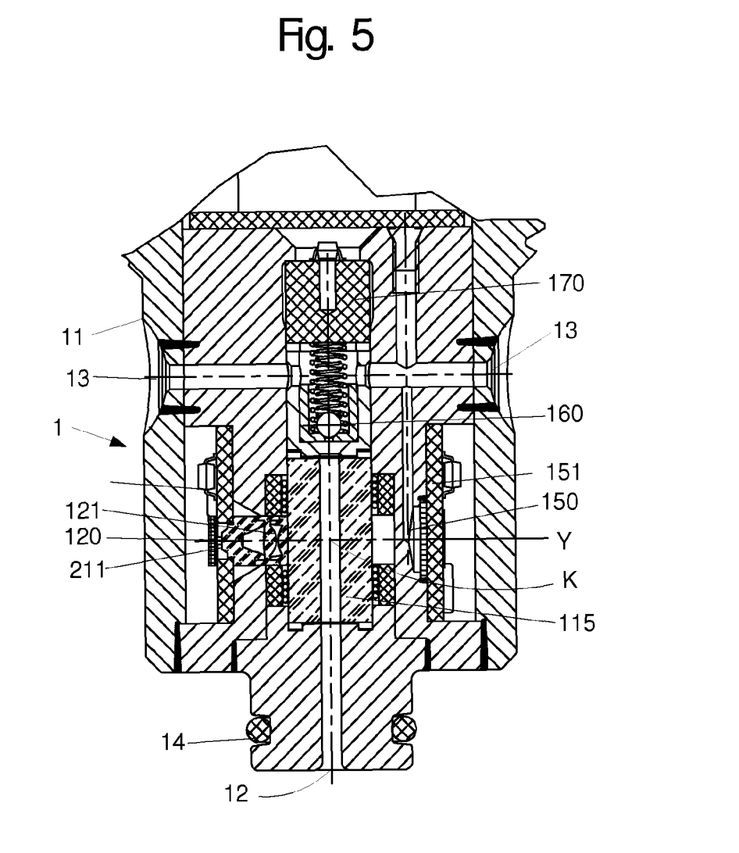
FIG. 5 shows a cross section through an extended sensor.

FIGS. 4 and 5 show in each case a section through a sensor 1. In the sensor body 11, which is sealed off by way of the seal 14, the measurement cylinder 115 is accommodated coaxially, in which the capillary tube C is located. The medium is guided into said capillary tube, via the inlet 12, into the inspection space K.

FIG. 4 illustrates the main light direction with the optical axis Z, which runs through the inspection space K. On one side, the light source 110 with a diverging lens 120 and a converging lens 121 is arranged. Opposite thereto is the first optical detector 111 which has the same lens arrangement. The light source 110 is driven by the light control circuit board 130 and the first optical detector 111 by the light evaluation circuit board 140.

FIG. 5 illustrates the scattered light direction with the optical axis Y, which leads to a scattered light detector 211. Said detector has the same lens arrangement with the diverging lens 12 and the converging lens 121 as the light source.

An essential feature for the miniaturization of a construction of the sensor 1 that is configured to be cylindrical is the shortened distance between light source 110 (object plane) and the illumination maximum in the inspection space center K (image plane), since this construction size is aligned diametrically to the symmetry axis of the cylindrical sensor 1 and thus directly determines the diameter. The distance of the object to the image (projection distance) is composed, in an imaging system with a real image, of the partial distances of object to main plane H of the objective (object width) and the distance of the image to the main plane H (image width), wherein the distances have a reciprocal relationship to the imaging scale. $1/g + 1/b = 1/f$, wherein $\beta = B/G$. (1) A limitation is given by the image width being determined mainly through the thickness of the pressure-stable wall of the measurement cylinder 115 toward the capillary tube C and being determined by the provided maximum pressure with which the sensor is intended to be operated. An advantageous configuration of the wall of the measurement cylinder 115, which must be optically transparent for light in the applied wavelength range from infrared to ultraviolet, is achieved by it being produced from thermally or chemically prestressed glass. For the construction to remain symmetrical and so that as many identical parts as possible are brought about for achieving low production costs, the projection system of the light source 110 is used as the imaging system for the detector 111 by swapping the object plane and image plane. In order to achieve the shortening of the distance necessary for miniaturization, a novel objective construction is chosen which effects a significant shift of the main plane in the direction of the image plane. This is achieved by initially producing using a diverging lens 120 an upright virtual intermediate image which is located in the z-direction in front of the item/object and is thus located closer to the main plane than the object, but strongly decreased in size. This virtual intermediate image is projected invertedly onto the image plane via at least one converging lens 121, wherein the imaging equation (1) with the object width works with the virtual operating image.

In a particularly advantageous configuration of the proposed solution, a reduction in size of the image of the light source in the inspection space K is aimed for, since in that way the optically active surface of the light source, which is preferably a light-emitting semiconductor structure, can be increased in terms of size, and thus an overall higher luminous flux can be produced with a current density in the semiconductor crystal which remains the same and which is limited in principle and additionally deterministic for its service life. Also, rougher semiconductor structures are easier to produce and bring a high yield and thus result in low costs per piece.

The lens system consists of lenses of the light source 110 and lenses of the optical detector 11. In one configuration, the semiconductor chip of the light source 110 is optically cemented with the first surface of a diverging lens 121, which requires that this first surface has a planar design. The advantage is both the avoidance of two transitions of optical materials with significantly different refractive indices and the associated light losses through reflection, and the avoidance of the reduction of the luminance through the transition of the light from semiconductor material with a high refractive index to a medium (gas, vacuum) with low refractive index, and also the simultaneous hermetic seal of the semiconductor surface and the savings of the otherwise associated additional costs. This is particularly important for the transition from the material of the light source to the subsequent material, which in a preferred embodiment consists of gallium arsenide as base material, which has refractive indices of greater than 3. A further significant influence factor for achieving as little optical construction length as possible is a small focal length of the optical system with a simultaneously high MTF, which is preferably purely diffraction-limited, over the entire image height. In a preferred embodiment, this is achieved by using more than one converging lens 121 behind the diverging lens 120, which produces the inverted real image from the upright virtual intermediate image.

In a further advantageous embodiment of the proposed solution, the last optically effective surface of the last converging lens 121 of the objective before the cylinder surface of the tubular wall of the measurement cylinder 115 is of planar design, and the intermediate space to this surface and the tubular wall is filled with an optically transparent material which has the same or approximately the same refractive index as the material of which the tube wall consists, preferably a polymer which cures under light exposure and/or heat exposure. Owing to the adapted refractive index of the filling material, no or no substantial refraction occurs at the boundary surface of polymer and tubular wall. A further advantage of this configuration is the avoidance of two optical transitions from air to higher-refractive material (for example glass), as a result of which the reflection losses are further reduced. In an optical projection system according to the invention, which consists of in each case at least one diverging lens 120 and of in each case at least one converging lens 121, the number of transitions of air/glass is only 2.

In a further advantageous configuration of the proposed solution, the light source is imaged only in the region of the optical axis Z in a diffraction-limited manner—that is to say with as good an MTF as possible—and with increasing distance from the optical axis z in the xy direction with continuously decreasing MTF, wherein the respective zone of the highest MTF in the z direction remains always in the image plane, that is to say the image plane is not curved. This is achieved by configuring preferably all optical surfaces—with the exception of the planar surfaces—as aspheres which can consist in a further configuration also as Fresnel surfaces or of GRIN material or of combinations thereof. The controlled reduction of the MTF leads to the particles of every size achieving their maximum shading and thus their respective maximum signal height only if they move through the inspection space exactly along the x-axis with the fluid.

In a preferred configuration of this optical construction, the drop of the MTF in the image plane follows the function $1/\text{root}(a^2 4r^2+1)$, wherein r is the distance from the optical axis z in the image plane, and a is greater than or equal to the wavelength λ of the light of the light source 110. When using a linear Lambert emitter as a light source, as is the case for example in semiconductor crystals, for the luminance in the image plane a hyperbolic-Gaussian radiation distribution results, wherein the image plane is defined by the xy plane of the Cartesian coordinate system with the origin through the z axis.

Particles which pass parallel to but away from the x-axis through the inspection space K produce a weakened signal because they pass through regions of lower luminance with respect to the maximum signal which they produce if their movement path extends coaxially to the x-axis. Despite the varying luminance, there is a linear relationship between particle size and maximum signal height at the location x=0, y=0 and z=0, for particles the diameter of which is greater than a.

In a further advantageous configuration of the proposal according to the invention, only those particles are taken into consideration for counting of which the size is within the linear characteristic curve region and of which the relationship of maximum signal height to delay, measured at 50% of the vertex value, between a threshold value which is preferably at 25% of the ratio of the maximum signal height to the delay does not fall below a determined settable lower limit. Here, a flow rate of the fluid that is constant during the short signal and thus of the particle in the inspection space K is assumed.

Figure 6:
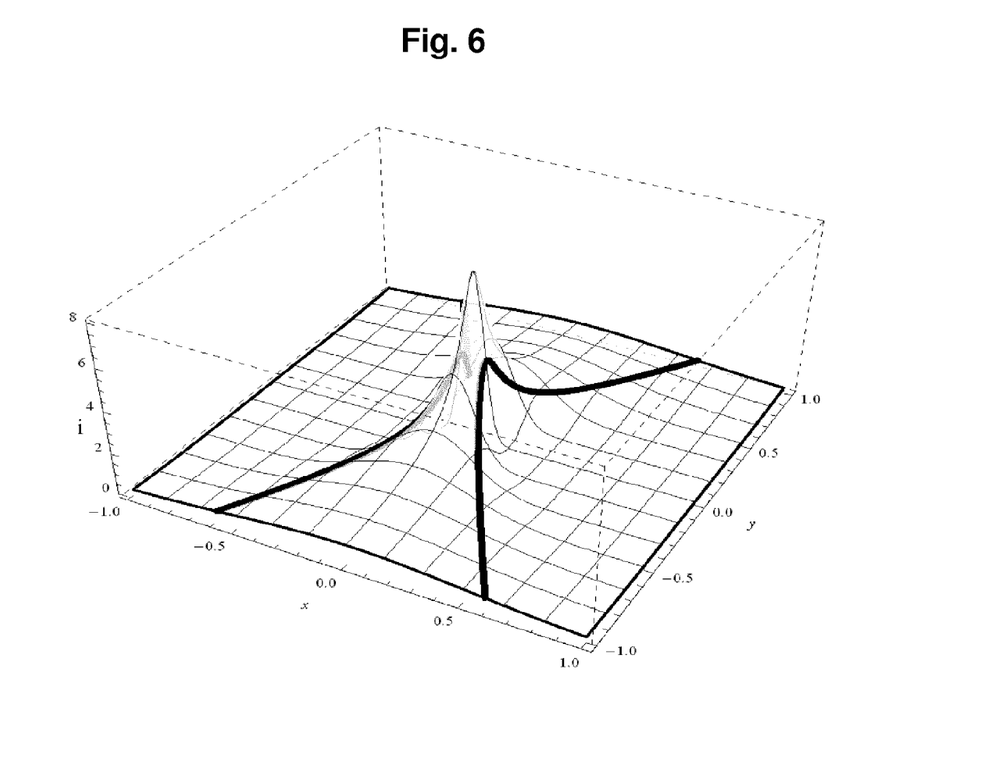
FIG. 6 shows an intensity diagram of the light in the inspection space.

An intensity distribution i of the light in the inspection space is illustrated in FIG. 6, wherein the center of the inspection space is at the point x=0.0 and y=0.0. The intensity i follows a hyperbolic-Gaussian intensity distribution in the xy plane according to the formula $$i = \frac{2e^{-\frac{x^2}{2\left(\frac{1}{2}\sqrt{a^2+\frac{4y^2}{b^2}}\right)^2}}}{\sqrt{a^2+\frac{4y^2}{b^2}}\sqrt{2\pi}} \qquad (2)$$

wherein a is the tangential minimum distance of the hyperbolas and b is the slope of the asymptotes of the hyperbolas.

Figure 7:
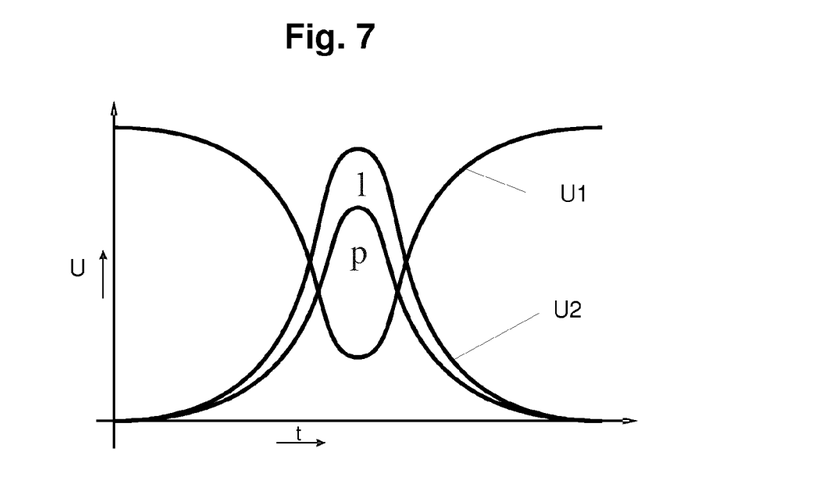
FIG. 7 shows a diagram of the evaluation voltages at the optical detectors.

FIG. 7 shows evaluation voltages U at the optical detectors over time t while a particle p passes through the inspection space. The curve U1 shows the signal of the first optical detector. A particle p effects shading and thus a dropping and re-increasing curve U1.

The curve U2 shows the output signal of a scattered light detector. For a particle p, a signal up to a maximum height is produced, depending on the surface of the particle p. If air bubbles l are located in the medium, significantly higher scatter signals are produced. This enables differentiation between particles p and air bubbles l.

For further characterization of the particles, in the configuration of the sensor according to FIG. 5, a pressure measurement apparatus 150, possibly combined with a temperature measurement apparatus, and a humidity measurement apparatus 170 are also installed. The humidity measurement apparatus 170 evaluates the water content of the medium by microwave absorption.

Figure 8:
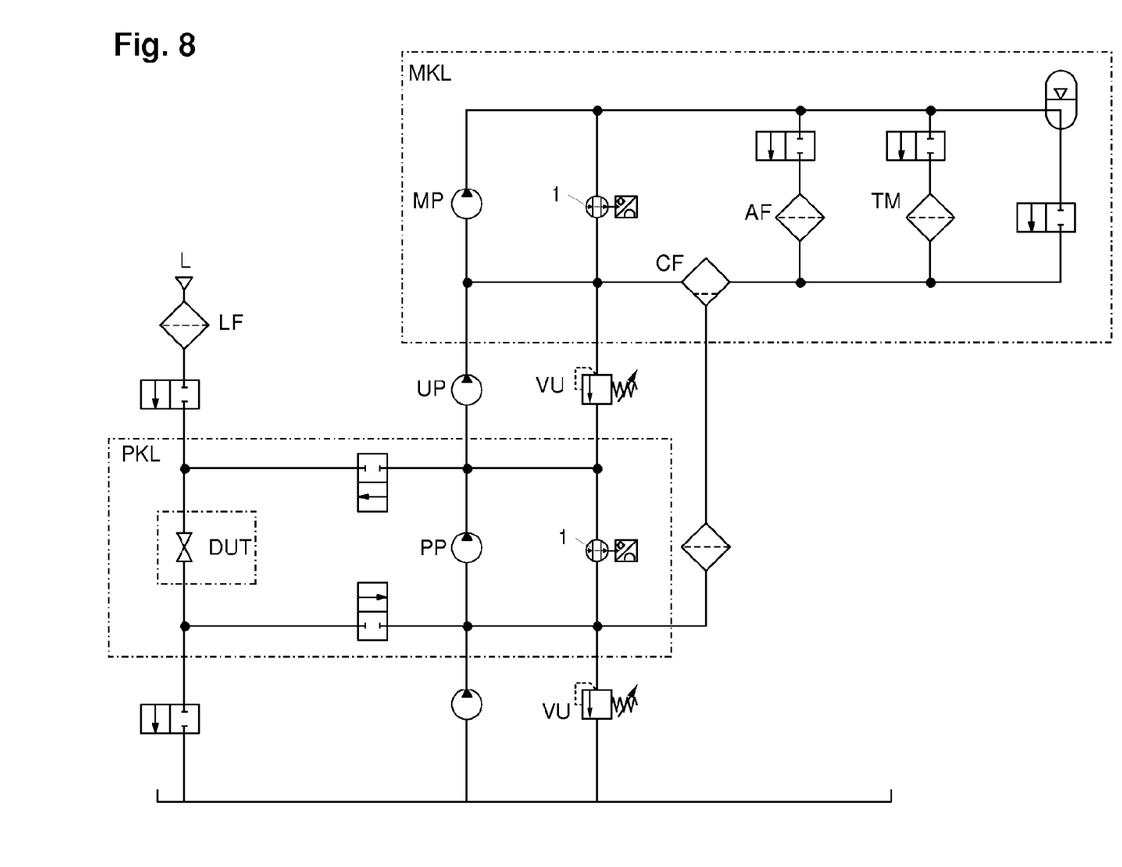
FIG. 8 shows a schematic diagram of a test and measurement system.

FIG. 8 shows a schematic illustration of a test circuit PKL and a measurement circuit MKL, which are both equipped with a sensor 1. The medium, typically hydraulic oil, can flow through the device under test DUT using the test pump PP. Here, the sensor 1 is located in a secondary connection to the test pump PP and analyzes the contamination of the oil flowing through the device under test DUT. With a corresponding setting of the valves, the medium can be transferred using the transferring pump UP from the test circuit PKL into the measurement circuit MKL. In the measurement circuit, the oil can then be squeezed through the crossflow filter CF using the measurement pump MP, wherein the thus circulating suspension of oil and particles, which come from the test circuit, is continuously concentrated. Here, too, the sensor 1 is arranged in the secondary connection to the measurement pump MP and can test the thus circulating suspension. Once the particle concentration in the measurement circuit has achieved a specified extrapolatable limit value, which corresponds in relation to the circulating fluid volume to the contamination degree of the device under test DUT, the measurement cycle is complete. The suspension is thereafter guided through corresponding switching of the valves through the absolute filter AF and is thus completely removed from the circuit. It is also possible for the medium to be squeezed through a test membrane TM. Here, all the particles then remain on the filter TM and can be documented externally. While the particles in the filters are removed from the hydraulic oil, the contamination decreases correspondingly. The purified hydraulic oil can then, after corresponding setting of the valves, be squeezed back again into the test circuit PKL via the CF filter. All pumps are protected in the case of a blockade in the circuits by way of an overpressure valve UV. It is also possible for air L to be blown through the device under test DUT with corresponding setting of the valves once the measurement is complete. To this end, the air L passes via the air filter LF through the device under test DUT. Any remaining rests of the hydraulic oil are then conducted away into a tank.

Figure 9:
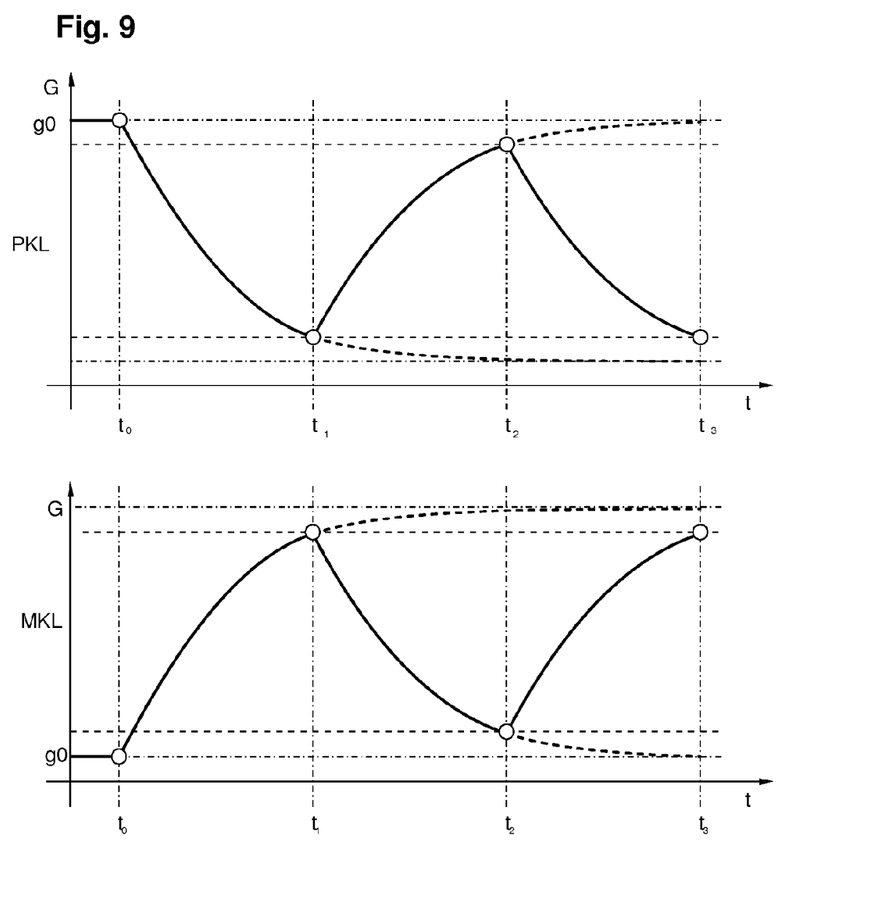
FIG. 9 shows the diagrams of the contamination degrees in a test and measurement system.

The profile of the contamination degree G in the test circuit PKL and the measurement circuit MKL over time t is illustrated in FIG. 9. In the test circuit PKL, initially a high starting value g0 of the contamination degree G is present, which is introduced by the contamination of the device under test. Once the medium is transferred from the test circuit to the measurement circuit and is replaced by cleaned medium from the CF filter, the contamination degree G in the test circuit PKL decreases. In parallel, in the measurement circuit MKL, the contamination degree G is initially at a low value g0 and increases. Once the maximum contamination degree in the test circuit becomes sufficiently exactly detectable through extrapolation of the time profile, the measurement is over and the valves are switched by the filters Af or TM such that the contamination degree G in the measurement circuit MKL decreases. This change is continued.

For better illustration of the processes, this can be shown on a display with a non-linear time axis.

Figure 10:
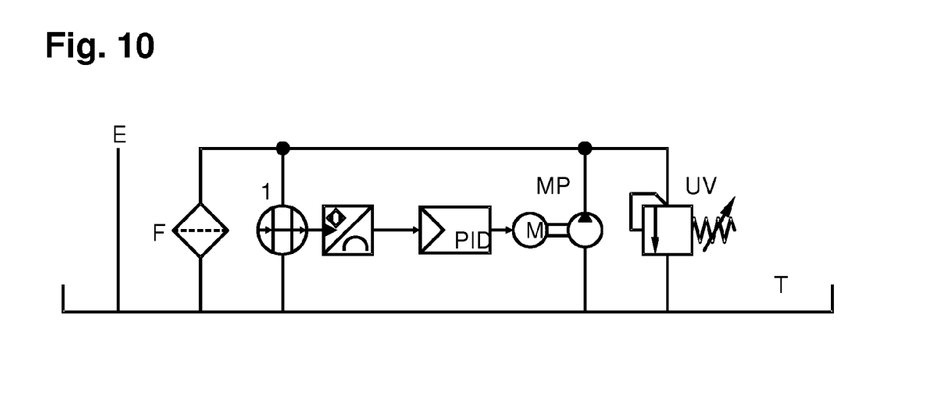
FIG. 10 shows a schematic diagram of a hydraulic oil cleaning system.

FIG. 10 illustrates the use of the sensor 1 in a cleaning apparatus. The medium is squeezed from the tank T through the filter F by the measurement pump MP, cleaned therewith and guided back into the tank T. In the secondary connection to the measurement pump MP and the filter F is the sensor 1, which checks the contamination degree G in the circuit. In dependence on the contamination degree G, the motor of the measurement pump MP is controlled by the regulator PID. Here, too, the measurement pump MP is protected by an overpressure valve UV.

A cleaned medium can be removed from the tank T via the removal line E.

Figure 11:
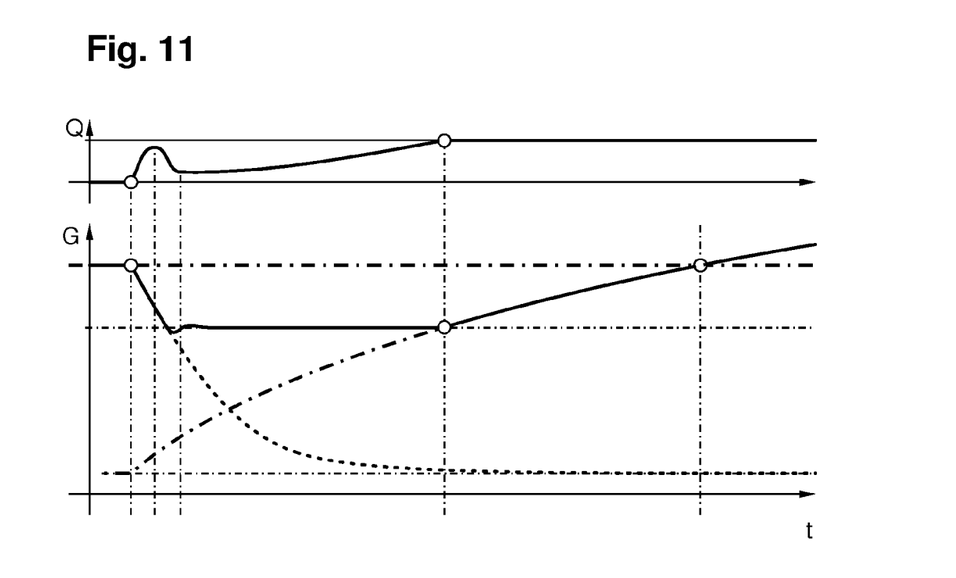
FIG. 11 shows diagrams relating to the hydraulic oil cleaning system.

FIG. 11 illustrates the volume flow Q resulting in the cleaning apparatus through the measurement pump MP over the contamination degree G. The initially high contamination degree G falls to a predetermined non-critical value. This value is then kept constant by the regulator. When the volume flow is not sufficient to decrease the contamination, the contamination degree increases again. If this stage which is indicated by the sensor is reached, a filter change must be carried out.

Figure 12:
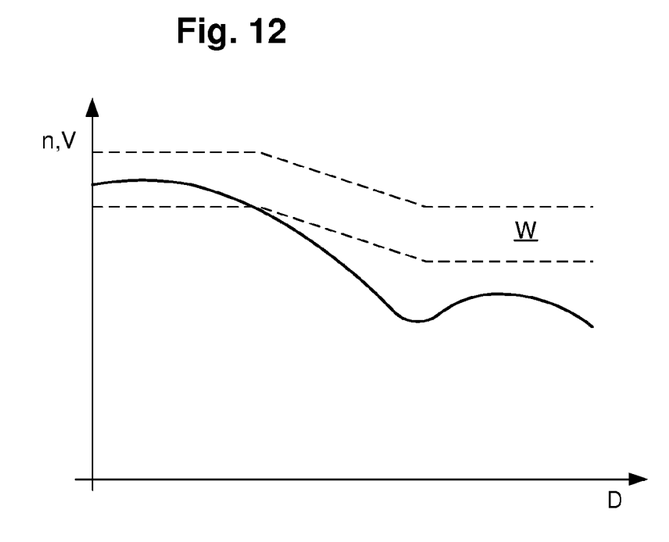
FIG. 12 shows a diagram relating to the warning region in dependence on the diameter and the concentration of the particles.

FIG. 12 shows a diagram for illustrating the evaluation of the signals of the sensor. Advantageously, the sensor signals are amplified and made acoustically perceivable using a loudspeaker. The sensor signal can here be fitted into the audible frequency range by transformation.

Plotted is a warning region W which indicates when, in dependence on the diameter D and the associated concentration of the particles, a warning is output. The concentration of the particles can be determined from the number of particles with the corresponding diameter D of the particles or the volume V of the measured particles with the diameter D. However, different parameters such as the sum diameter of the particles or their sum surface area can also be used. It is assumed in this diagram that, with small diameters D, the warning region only responds at larger numbers n or a larger volume V, while it responds earlier with larger diameters of the particles, for example because there is a greater risk of blockage of the device. Here, the warning region W is either kept neutral, or, following an arbitrary but determined function, fulfills the requirements of a specific facility in respect of the contamination limits that must be observed and are necessary therefor.

Figure 13:
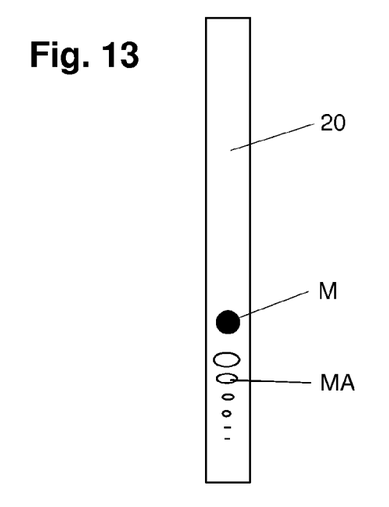
FIG. 13 shows a calibration standard.

FIG. 13 shows a transparent calibration standard 20 with different marks at defined heights. If the calibration standard is inserted into the inspection space of the sensor at a defined height, it is possible to check how the sensor responds. For example, optical markings MA of different sizes can be etched onto the calibration standard. Metallically defined reflective markings M also make sense, since thereby the scattered light detectors can be checked.

REFERENCE SIGNS 1 sensor
11 sensor body
12 inlet
13 outlet
14 inner seal
15 outer seal
16 screw-in thread
17 drive
18 electrical connection
20 calibration standard
110 light source, LED
111 optical detector
112 stop
113 lenses of the light source
114 ring core
115 measurement cylinder
116 differential coil
117 lenses of the optical detector
118 stop of the optical detector
120 diverging lens
121 converging lens
130 light control circuit board
140 light evaluation circuit board
150 pressure measurement apparatus
151 pressure evaluation circuit board
160 pressure regulator
170 dielectric moisture measuring apparatus
211 scattered light detector
212 stop of the scattered light detector
213 lens of the scattered light detector
AF absolute filter
C capillary tube
CF CF filter
D diameter
DUT device under test
E removal line
F filter
G contamination degree
K inspection space
L air
LF air filter
M metallic marking
MA etched marking
MP measurement pump
MKL measurement circuit PID regulator
PKL test circuit
PP test pump
Q volume flow
PID regulator
T tank
UP transfer pump
UV overpressure valve
V volume
W warning region
X longitudinal axis of the capillary tube
Y scattered light axis
Z optical axis
g0 initial value of the contamination
i light intensity
l air bubble
n number
p particle
t time coordinate
x,y coordinates of the inspection space

The invention claimed is:

1. A sensor for measuring particles in a contaminated media, the sensor comprising:
   a capillary tube for conducting and measuring a medium;
   an optically transparent measurement cell having a shaft, through said measurement cell said capillary tube passes, said measurement cell being cylindrically shaped and said capillary tube extending coaxially;
   an optical lens system having a light source and at least one optical detector, said optical lens system having an optical axis aligned perpendicular to said capillary tube;
   said measurement cell having a center area defining an inspection space, on said inspection space said optical lens system with said light source and said at least one optical detector is focused; and
   two differential coils disposed coaxial to said capillary tube and on said shaft of said measurement cell, said two differential coils generating and detecting a coaxial magnetic alternating field form a magnetic detector, said differential coils being actuated such that a magnetic alternating field in said inspection space is canceled.

2. The sensor according to claim 1, wherein said capillary tube has a round cross section with a maximum diameter of 2 mm.

3. The sensor according to claim 1, further comprising a pressure measurement apparatus connected to said capillary tube via holes formed therein and measures a pressure of the medium in said capillary tube.

4. The sensor according to claim 3, further comprising a temperature measurement apparatus for measuring a temperature of the medium in said capillary tube.

5. The sensor according to claim 4, wherein said temperature measurement apparatus is integrated in said pressure measurement apparatus.

6. The sensor according to claim 1, wherein said measurement cell is configured to be pressure-stable.

7. The sensor according to claim 1, further comprising a cylindrical housing having a cylinder wall, a front-end opening and a duct, said measurement cell is accommodated coaxially in said cylindrical housing and the medium flows into said capillary tube through said front-end opening and leaves at an end of said capillary tube perpendicular to said cylinder wall of said cylindrical housing through said duct.

8. The sensor according to claim 7, wherein the sensor can be inserted into a standard hole of a hydraulic device.

9. The sensor according to claim 1, wherein said optical lens system further comprises a diverging lens and a converging lens, which are disposed in each case in front of said light source and in front of said optical detector.

10. The sensor according to claim 1, wherein said optical detector has an associated lens system and said optical detector with said associated lens system is disposed in the optical axis.

11. The sensor according to claim 10, further comprising at least one scattered light detector disposed perpendicular to said optical detector with said associated lens system.

12. The sensor according to claim 1, wherein said light source is formed by an LED emitting linear light.

13. The sensor according to claim 12, wherein said LED is configured in combination with a converging lens and a stop.

14. The sensor according to claim 1, wherein said optical detector is one of a plurality of optical detectors, said optical detectors are configured with at least one photodiode and a combined lens and stops.

15. The sensor according to claim 1, wherein said two differential coils are excited with opposite radio-frequency currents such that at any time point a magnetic field strength in a center of said inspection space equals zero.

16. The sensor according to claim 1, further comprising a moisture measuring apparatus which makes a water content of the medium measurable by way of microwave absorption.

17. The sensor according to claim 1, further comprising a calibration standard on an optically and/or magnetically transparent carrier, on said calibration standard microstructures are applied by lithography which are within a size region and form of particles to be detected.

18. A method for measuring particles in a medium with a sensor according to claim 1, which method comprises the steps of:
   squeezing the medium through the capillary tube at a defined flow quantity;
   capturing an image of a particle when the particle passes through the inspection space via the optical detector;
   detecting via the magnetic detector whether a magnetizable particle is present;
   counting a number of the particles detected; and
   evaluating a size thereof.

19. The method according to claim 18, which further comprises detecting via scattered light detectors whether gas bubbles are included in the medium.

20. The method according to claim 18, which further comprises determining on a basis of a strength of signals measured at the optical detector whether gas bubbles are included in the medium.

21. The method according to claim 18, which further comprises outputting a warning signal when at least one of a detected particle number or size are exceeded in a unit time.

22. The method according to claim 18, which further comprises amplifying sensor signals and making the sensor signals acoustically perceivable using a loudspeaker.

23. The method according to claim 22, which further comprises fitting a frequency region of a sensor signal into an audible frequency region by transformation.

24. The method according to claim 18, wherein a representation of measurement values takes place on a display with a non-linear time axis.

25. The method according to claim 18, which further comprises calibrating the sensor by inserting a calibration standard into the capillary tube, the calibration standard having at least one of optical or magnetic markings on at least one of an optically or magnetically transparent carrier, which produce in the inspection space such optical and/or magnetic effects as particles.

26. A testing method, which comprises the steps of:
providing a sensor according to claims 1;
inserting the sensor into a test circuit for hydraulic components; and
determining a contamination degree of the hydraulic components.

27. An operating method, which comprises the steps of:
providing a sensor according to claim 1; and
inserting the sensor into a cleaning apparatus for a hydraulic medium.

\* \* \* \* \*